(12) United States Patent
Nukanobu

(10) Patent No.: US 12,127,868 B2
(45) Date of Patent: Oct. 29, 2024

(54) MOBILE RADIOGRAPHIC IMAGING APPARATUS, STORAGE MEDIUM, METHOD, CONTROL APPARATUS, AND RADIOGRAPHIC IMAGING SYSTEM

(71) Applicant: Konica Minolta, Inc., Tokyo (JP)

(72) Inventor: Takeshi Nukanobu, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 364 days.

(21) Appl. No.: 17/549,452

(22) Filed: Dec. 13, 2021

(65) Prior Publication Data

US 2022/0183639 A1 Jun. 16, 2022

(30) Foreign Application Priority Data

Dec. 14, 2020 (JP) .................................. 2020-206610
Dec. 14, 2020 (JP) .................................. 2020-206641

(51) Int. Cl.
*A61B 6/00* (2024.01)
*A61B 6/46* (2024.01)

(52) U.S. Cl.
CPC ............ *A61B 6/4405* (2013.01); *A61B 6/463* (2013.01); *A61B 6/542* (2013.01)

(58) Field of Classification Search
CPC ....... A61B 6/4405; A61B 6/542; A61B 6/463; A61B 6/486; A61B 6/54; A61B 6/5211; A61B 6/461; A61B 6/04; A61B 6/488; A61B 6/4464; A61B 6/5264; A61B 6/52; A61B 6/40; A61B 6/4452; A61B 6/467; A61B 6/482; A61B 6/563; A61B 6/5241; A61B 6/545; A61B 6/56; A61B 6/465; A61B 6/548; A61B 6/469; A61B 6/4283; A61B 2560/0456; A61B 6/4291;
(Continued)

(56) References Cited

U.S. PATENT DOCUMENTS

2018/0368797 A1* 12/2018 Kuwata ................ A61B 6/5217
2019/0246999 A1* 8/2019 Liu ......................... A61B 6/487
(Continued)

FOREIGN PATENT DOCUMENTS

JP 2003290184 A 10/2003
JP 2010179155 A 8/2010
(Continued)

OTHER PUBLICATIONS

JPO Notification of Reasons for Refusal for corresponding JP Application No. 2020-206610; Date of Mailing, Jan. 4, 2022.
(Continued)

*Primary Examiner* — Irakli Kiknadze
(74) *Attorney, Agent, or Firm* — CANTOR COLBURN LLP

(57) ABSTRACT

A mobile radiographic imaging apparatus performs dynamic imaging by using radiation to obtain a dynamic image constituted of multiple frames and performs still imaging by using radiation to obtain a still image constituted of a single frame. The apparatus includes a first hardware processor that allows the apparatus to perform the dynamic imaging in which a mAs per frame is less than 0.1 mAs and that does not allow the apparatus to perform the still imaging in which a mAs per frame is less than 0.1 mAs.

17 Claims, 3 Drawing Sheets

(58) Field of Classification Search
CPC ..... A61B 6/4411; A61B 6/5205; A61B 6/566; G01T 1/161; H04N 5/32; H04N 23/30; H04W 28/06
USPC ......................................................... 378/98.8
See application file for complete search history.

(56) References Cited

U.S. PATENT DOCUMENTS

2020/0100754 A1* 4/2020 Uehara ................ A61B 6/5211
2020/0222018 A1* 7/2020 van Walsum .......... A61B 6/463

FOREIGN PATENT DOCUMENTS

| JP | 2012110399 A | 6/2012 |
| JP | 2013070866 A | 4/2013 |
| JP | 2018007851   | 1/2018 |

OTHER PUBLICATIONS

JPO Notice of Reasons for Refusal for corresponding JP Application No. 2020-206641; Issued Jun. 25, 2024; 12 pages.

* cited by examiner

MOBILE RADIOGRAPHIC IMAGING APPARATUS, STORAGE MEDIUM, METHOD, CONTROL APPARATUS, AND RADIOGRAPHIC IMAGING SYSTEM

CROSS-REFERENCE TO RELATED APPLICATIONS

The present invention claims priority under 35 U.S.C. § 119 to Japanese Patent Application Nos. 2020-206610 and 2020-206641 both filed on Dec. 14, 2020, the entire contents of which being incorporated herein by reference.

BACKGROUND

Technological Field

The present disclosure relates to a mobile radiographic imaging apparatus, a storage medium, a method, a control apparatus, and a radiographic imaging system.

Description of the Related Art

A radiographic imaging system that includes a radiation detector and an irradiation device is used to perform radiographic imaging. To perform radiographic imaging, the mAs needs to be set in the radiographic imaging system. The mAs is the product of the tube current and the irradiation time. The tube current refers to the current flowing through the radiation source of the irradiation device.

A known radiographic imaging system, such as the system disclosed in JP2013-70866A, sets the mAs according to the operation manually made by a user (e.g., radiologist) on an operation panel.

SUMMARY

In recent years, dynamic imaging has been performed to obtain a dynamic image constituted of multiple frames.

Although the number of frames differs between dynamic imaging and still imaging, it is desirable that the exposure dose in dynamic imaging conform to the Diagnostic Reference Levels guideline (DRLs) in still imaging. To perform dynamic imaging in conformity with the DRLs, the exposure dose per frame needs to be considerably lower than the exposure dose in still imaging.

It is known that the longer the distance between the radiation source and the radiation detector (SID) is, the lower the exposure dose is and that the shorter the SID is, the greater the exposure dose is. It is therefore desirable that the SID be as great as possible in dynamic imaging.

However, imaging a lying subject or imaging with a mobile medical vehicle may not ensure as great the SID as the SID in imaging a standing subject in a radiography room. For example, the exposure dose with the SID of only 100 centimeters is three times greater than the exposure dose with the SID of 180 centimeters, which is the standard SID when a standing subject is images in a radiography room. This increases the possibility that the exposure dose is far beyond the DRLs.

In addition, when a radiation source (tube) for emitting radiation generates a large amount of radiation, the heat unit value thereof may reach the upper limit and the radiation source may not emit radiation thereafter.

The upper limit of the heat unit value for the radiation source in the mobile medical vehicle is generally lower than the upper limit of the heat unit value for the radiation source in the radiography room.

When dynamic imaging is performed using the mobile medical vehicle under the same condition as the imaging in the radiography room, the heat unit value reaches its upper limit earlier than when imaging is performed in the radiography room, owing to heat generated by the radiation source. As a result, imaging may not be performed thereafter.

The present invention has been conceived in view of the above issue. Objects of the present invention include enabling appropriate dynamic imaging, which is performed for obtaining a dynamic image constituted of multiple frames, even when the distance between the radiation source and the radiation detector is limited or when the upper limit of the heat unit value of the radiation source is limited.

To achieve at least one of the abovementioned objects, according to an aspect of the present invention, there is provided a mobile radiographic imaging apparatus that performs dynamic imaging by using radiation to obtain a dynamic image constituted of multiple frames and that performs still imaging by using radiation to obtain a still image constituted of a single frame, the apparatus including: a first hardware processor that allows the apparatus to perform the dynamic imaging in which a mAs per frame is less than 0.1 mAs and that does not allow the apparatus to perform the still imaging in which a mAs per frame is less than 0.1 mAs.

To achieve at least one of the abovementioned objects, according to another aspect of the present invention, there is provided a non-transitory computer-readable storage medium storing a program that controls a mobile radiographic imaging apparatus configured to perform dynamic imaging by using radiation to obtain a dynamic image constituted of multiple frames and configured to perform still imaging by using radiation to obtain a still image constituted of a single frame, wherein the program allows the apparatus to perform the dynamic imaging in which a mAs per frame is less than 0.1 mAs, and the program does not allow the apparatus to perform the still imaging in which a mAs per frame is less than 0.1 mAs.

To achieve at least one of the abovementioned objects, according to another aspect of the present invention, there is provided a method for controlling a mobile radiographic imaging apparatus that performs dynamic imaging by using radiation to obtain a dynamic image constituted of multiple frames and that performs still imaging by using radiation to obtain a still image constituted of a single frame, the method including: allowing the apparatus to perform the dynamic imaging in which a mAs per frame is less than 0.1 mAs, and not allowing the apparatus to perform the still imaging in which a mAs per frame is less than 0.1 mAs.

To achieve at least one of the abovementioned objects, according to another aspect of the present invention, there is provided a control apparatus of an irradiation apparatus that emits radiation for dynamic imaging in which a dynamic image constituted of multiple frames is obtained and for still imaging in which a still image constituted of a single image is obtained, the control apparatus including: a hardware processor that allows the dynamic imaging in which a mAs per frame is less than 0.1 mAs and that does not allow the still imaging in which a mAs per frame is less than 0.1 mAs.

To achieve at least one of the abovementioned objects, according to another aspect of the present invention, there is provided a mobile radiographic imaging apparatus capable of performing still imaging to obtain a still image constituted of a single frame and dynamic imaging to obtain a dynamic image constituted of multiple frames, the mobile radiographic imaging apparatus including: a hardware processor that sets an imaging condition on a mAs per frame in the still imaging and a mAs per frame in the dynamic imaging, wherein a lower limit of the mAs per frame in the dynamic imaging is lower than a lower limit of the mAs per frame in the still imaging.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein.

DETAILED DESCRIPTION OF THE EMBODIMENTS

Hereinafter, one or more embodiments of the present invention will be described with reference to the drawings. However, the scope of the invention is not limited to the disclosed embodiments.

<1. Configuration of Radiographic Imaging System>

Figure 1:
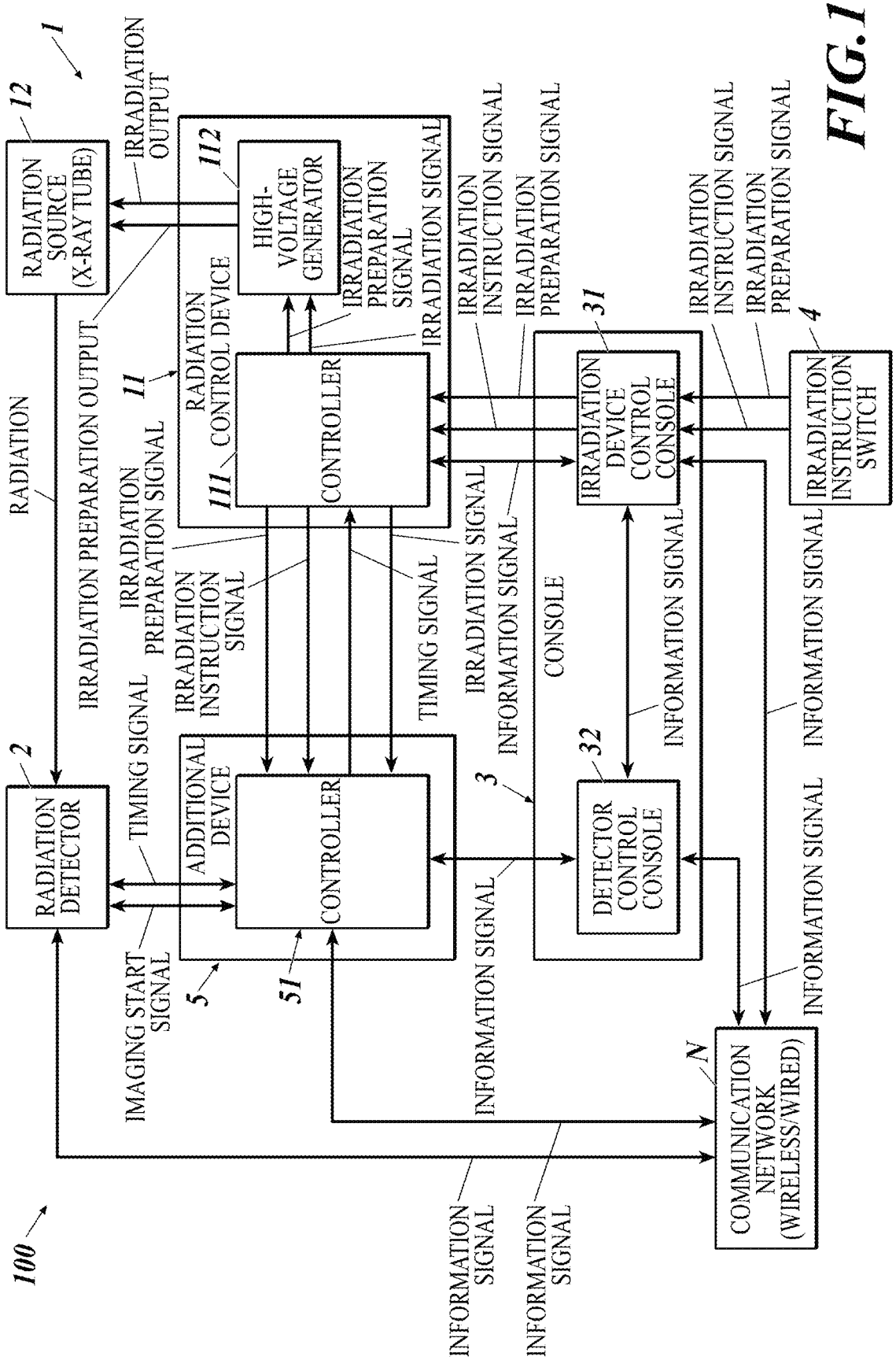
FIG. 1 is a block diagram showing a radiographic imaging system according to an embodiment of the present invention.
Figure 2:
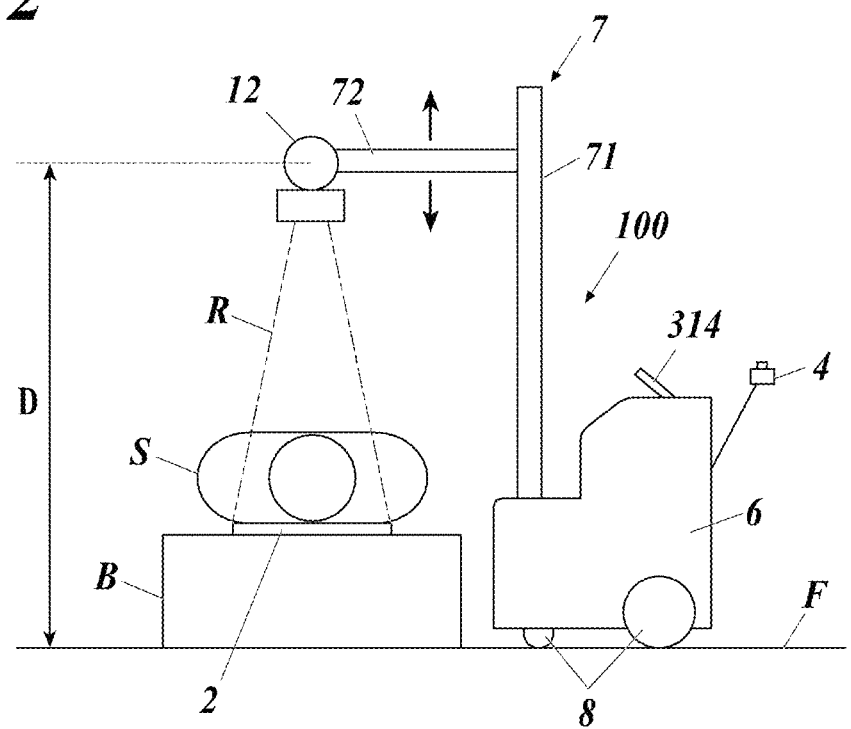
FIG. 2 is a lateral view of an example configuration of the radiographic imaging system in FIG. 1.
Figure 3:
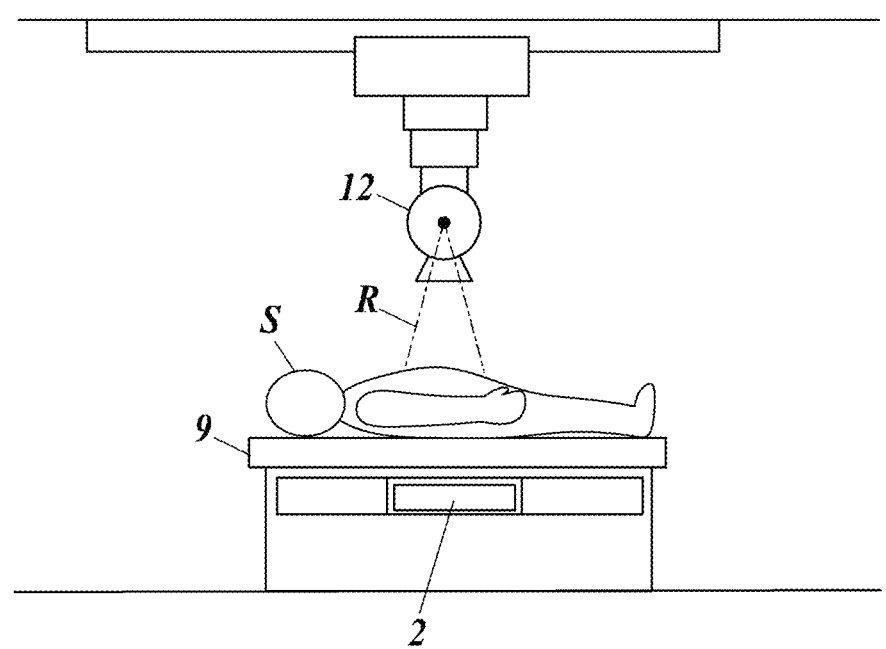
FIG. 3 is a lateral view of another example configuration of the radiographic imaging system in FIG. 1.

A schematic configuration of a radiographic imaging system (hereinafter, system 100) according to an embodiment is described. FIG. 1 is a block diagram showing the system 100. FIG. 2 is a lateral view of an example configuration of the system 100. FIG. 3 is a lateral view of another example configuration of the system 100.

The system 100 includes an irradiation device (hereinafter, irradiation device 1), a radiation detector (hereinafter, detector 2), and a console 3, as exemplified in FIG. 1.

The system 100 in this embodiment further includes an irradiation instruction switch (hereinafter, switch 4) and an additional device 5.

The system 100 may be able to communicate with the radiology information system (RIS) and the picture archiving and communication system (PACS) over a communication network N, such as the local area network (LAN), wide area network (WAN), or the Internet.

[1-1. Irradiation Device]

The irradiation device 1 emits radiation.

The irradiation device 1 includes a radiation control device 11 and a radiation source 12.

The radiation control device 11 includes a controller 111 (second hardware processor) and a high-voltage generator 112.

These components 111, 112 are electrically connected.

The controller 111 controls the radiation source 12 on the basis of imaging conditions that are set by the controller 311 (first hardware processor) of the irradiation device control console 31, which is described in detail later.

More specifically, when an irradiation preparation signal that is input to the controller 111 from the irradiation device control console 31 is turned on, the controller 111 turns on an irradiation preparation signal that is output to the high-voltage generator 112 and the additional device 5.

Further, when an irradiation instruction signal that is input to the controller 111 from the irradiation device control console 31 is turned on, the controller 111 turns on the irradiation instruction signal that is output to the additional device 5, and the controller 111 also sends an irradiation signal to the high-voltage generator 112. The irradiation signal corresponds to the imaging conditions set by the irradiation device control console 31.

When the irradiation preparation signal being input from the controller 111 is turned on, the high-voltage generator 112 outputs an irradiation preparation output to the radiation source 12.

Further, when the high-voltage generator 112 receives the irradiation signal from the controller 111, the high-voltage generator 112 applies a predetermined tube voltage as an irradiation output to the radiation source 12 and supplies the radiation source 12 with a predetermined amount of irradiation current (tube current).

The radiation source 12 (tube) emits radiation.

The radiation source 12 in this embodiment generates radiation (e.g., X-rays) in response to being supplied with a predetermined amount of irradiation current from the high-voltage generator 112.

The irradiation device 1 as configured above generates radiation corresponding to the imaging conditions set beforehand, on the basis of the signal input by the irradiation device control console 31 (irradiation instruction switch 4 to be described later).

In generating a still image, the irradiation device 1 emits radiation only once per one press of the switch 4.

In generating a dynamic image, the irradiation device 1 repetitively emits radiation every time the irradiation device receives an irradiation timing signal from the additional device 5 while the switch 4 is pressed.

[1-2. Radiation Detector]

The detector 2 generates digital data of a radiographic image that shows an imaging part of a subject S.

The detector 2 in this embodiment is a portable flat panel detector (FPD).

More specifically, the detector 2 in this embodiment includes: a scintillator; a sensor substrate; a scanner; a reader; a controller; and a communicator, which are not illustrated. The scintillator generates light corresponding to the dose of received radiation. The sensor substrate includes semiconductor elements and switch elements that are arranged two-dimensionally (in a matrix). The semiconductor elements generate electric charges corresponding to the intensity of received light. The switch elements accumulate and discharge the electric charges. The scanner switches on and off of each switch element. The reader reads the amount of electric charges discharged from each pixel as signal values. The controller controls the components of the detector 2 and generates a radiographic image on the basis of the signal values read by the reader. The communicator sends the generated radiographic image, various signals, and so forth to the other devices (e.g., irradiation device 1, console 3) and receives various kinds of information and signals from the other devices.

The detector 2 generates a still image or a dynamic image by accumulating and discharging electric charges and reading signal values in synchronization with irradiation by the irradiation device 1.

In generating a still image, the detector 2 generates one still image per one time the switch 4 is pressed.

In generating a dynamic image, the detector 2 repetitively generates a frame constituting the dynamic image every time the detector 2 receives the imaging timing signal from the additional device 5 while the switch 4 is pressed.

The detector 2 sends data of the generated radiographic image to the console 3 as necessary.

The detector 2 may not include a scintillator, and the semiconductor elements may directly convert radiation into electric charges.

The detector 2 may be integrated with the irradiation device 1 (e.g., computer tomography (CT)).

[1-3. Console]

The console 3 includes the irradiation device control console 31 and a detector control console 32, as shown in FIG. 1.

These consoles 31, 32 are personal computers or devices of exclusive use.

The irradiation device control console 31 and the detector control console 32 may be integrated into one device.

(1-3-1. Irradiation Device Control Console)

The irradiation device control console 31 in this embodiment serves as a control apparatus.

The irradiation device control console 31 is described in detail later.

(1-3-2. Detector Control Console)

The detector control console 32 mainly controls the detector 2.

The detector control console 32 is also capable of setting subject information and imaging conditions to the detector 2. The subject information includes the name, sex, age, and physical feature of the subject.

The detector control console 32 is also capable of sending the subject information and the imaging conditions set to the detector 2 to the irradiation device control console 31.

The detector control console 32 is also capable of setting the operation of the additional device 5 to the additional device 5, such as the cycle and the number of times of outputting the irradiation timing signal and the imaging timing signal.

The detector control console 32 may or may not be configured to change the set frame rate according to the set accumulation time. The detector control console 32 may maintain the frame rate regardless of the accumulation time.

Further, the detector control console 32 may be configured to set the imaging conditions that are to be set to the irradiation device 1.

Further, the detector control console 32 may be configured to receive the imaging conditions, etc. that are input to the irradiation device control console 31.

[1-4. Irradiation Instruction Switch]

The switch 4 is for a person who performs imaging to instruct irradiation.

The switch 4 in this embodiment is configured to receive two stage operations. More specifically, when the switch 4 is pressed to the first stage, the switch 4 turns on the irradiation preparation signal that is output to the irradiation device control console 31. When the switch 4 is pressed to the second stage, the switch 4 turns on the irradiation instruction signal that is output to the irradiation device control console 31.

In FIG. 1, the switch 4 is connected to the irradiation device control console 31, wherein the irradiation preparation signal and the irradiation instruction signal output by the switch 4 are input to the controller 111 via the irradiation device control console 31. Instead, the switch 4 may be connected to the controller 111 so that the irradiation preparation signal and the irradiation instruction signal are directly input to the controller 111.

[1-5. Additional Device]

The additional device 5 includes a controller 51 and a not illustrated communicator.

The controller 51 includes a CPU and a RAM and centrally controls the operation of the components of the additional device 5.

The controller 51 reads various programs stored in a not-illustrated storage and loads the programs into the RAM. In accordance with the loaded programs, the controller 51 performs various processes.

The communicator obtains the irradiation preparation signal output by the switch 4 via the controller 111 (irradiation device).

The communicator also obtains the irradiation instruction signal output by the switch 4 via the controller 111 (irradiation device).

The communicator also receives an imaging start signal from the detector 2.

The imaging start signal is turned on when the detector 2 is ready for imaging. The imaging start signal is turned off when the detector is not ready for imaging.

The communicator is also capable of repetitively outputting the irradiation timing signal to the controller 111 at a predetermined frame rate (e.g., 15 times per second).

The additional device 5 as configured above is capable of repetitively outputting the irradiation timing signal to the controller 111 via the communicator at a predetermined cycle, on the basis of: the irradiation instruction signal obtained from the controller 111 via the communicator; and the imaging start signal input from the detector 2 via the communicator. The irradiation timing signal is an instruction to emit radiation.

The additional device 5 causes the communicator to output the imaging timing signal, which indicates the timing of taking a radiographic image, to the detector 2, on the basis of the timing of outputting the irradiation timing signal.

The additional device 5 in this embodiment is configured to repetitively output the imaging timing signal at the same cycle as the cycle of the irradiation timing signal.

The additional device 5 repetitively outputs the irradiation timing signal and the imaging timing signal until these signals are output by a predetermined number of times or until a predetermined period of time elapses after the initial output of these signals.

[1-6. Operation of Radiographic Imaging System]

In the system 100 as configured above, the console 3 sets imaging conditions. When the user then presses the irradiation instruction switch 4, the irradiation device 1 and the detector 2 start radiographic imaging.

In imaging for obtaining a still image, the detector 2 is switched to a state of accumulation for a predetermined accumulation time, and is then switched to a state of reading.

While the detector 2 is in the state of accumulation, the irradiation device 1 irradiates the subject S and the detector 2 behind the subject S with radiation at a predetermined dose for a predetermined irradiation time.

The detector 2 generates a still image that consists of a single frame.

In imaging for obtaining a dynamic image, the detector 2 repeats a series of actions of switching to the state of accumulation for the predetermined accumulation time and then switching to the state of reading at a predetermined frame rate.

The irradiation device 1 repetitively irradiates the subject S and the detector 2 behind the subject S with pulse radiation with a predetermined dose for a predetermined irradiation time, every time the detector 2 switches to the state of accumulation at the predetermined frame rate.

Irradiation device 1 and the detector 2 repeat the above actions until the detector 2 generates a predetermined maximum number of frames or until a predetermined imaging time elapses.

The detector 2 then generates a dynamic image that consists of multiple frames.

As described above, the system 100 in this embodiment is capable of performing imaging for obtaining a still image and a dynamic image.

Hereinafter, imaging for obtaining a still image is called still imaging, and imaging for obtaining a dynamic is called dynamic imaging.

[1-7. Configuration Example of Radiographic Imaging System]

The system 100 in this embodiment constitutes a mobile radiographic imaging apparatus (mobile medical vehicle).

The mobile radiographic imaging apparatus includes a casing 6 and an arm 7 as shown in FIG. 2, in addition to the above devices 1 to 5.

The mobile radiographic imaging apparatus in this embodiment further includes wheels 8.

The casing 6 houses the radiation control device 11, the console 3, and the additional device 5.

On the upper part of the casing 6, the display 314 of the console 3 is provided.

Outside the casing 6, the irradiation instruction switch 4 is provided.

The arm 7 in this embodiment includes a first arm 71 and a second arm 72. The first arm 71 extends upwards from the casing 6. The second arm 72 extends forward from the first arm 71 and can slide in the vertical direction.

An end of the second arm 72 supports the radiation source 12.

The maximum distance D between the floor F, which is in contact with the lower ends of the wheels 8, and the radiation source 12 is equal to or shorter than 200 centimeters. The maximum distance D is obtained when the second arm 72 is positioned at the upper end of the first arm 71.

In performing radiographic imaging with this mobile radiographic imaging apparatus, the detector 2 is positioned between the floor F and the radiation source 12. Accordingly, the distance (SID) between the radiation source 12 and the detector 2 is limited as compared with in imaging in a radiography room. That is, the SID is shorter than 200 centimeters.

For example, when the detector 2 is placed on the bed B, the SID may be around 100 centimeters.

The second arm 72 of the arm 7 may not slide along the first arm 71. Instead, the height of the radiation source 12 may be adjusted by expanding or contracting the entire arm 7, by rotating the entire arm 7 on the base end supported by the casing, or by bending the arm 7 in a middle part.

The mobile radiographic imaging apparatus may be mobile with a means other than the wheels 8. For example, the weight of the mobile radiographic imaging apparatus may be reduced so as to be carried by a person or mountable on a commercial dolly. For another example, the bottom surface of the casing 6 may be smooth so that the radiographic imaging apparatus can slide on the floor F.

The system 100 may be configured as shown in FIG. 3, wherein the radiation source 12 is installed so as to suspend from the ceiling and capable of emitting radiation downward (imaging the lying subject).

In imaging the lying subject using such a system 100, the detector 2 is placed on an imaging stand 9. As a result, the SID is limited as compared with the SID in imaging the standing subject.

[1-8. Radiographic Imaging System and Others]

The system 100 as described above may be capable of emitting radiation in a lateral direction to image the standing subject.

The system 100 may be configured to perform only dynamic imaging.

The system 100 may be configured to display, on a display connected in the system 100, a dynamic image generated by the detector 2 on a real-time basis (to perform fluoroscopy, for example).

In the system 100, the radiation control device 11 may be integrated with the additional device 5.

<2. Irradiation Device Control Console>

Next, the irradiation device control console 31 of the console 3 in the system 100 is described in detail.

Figure 4:
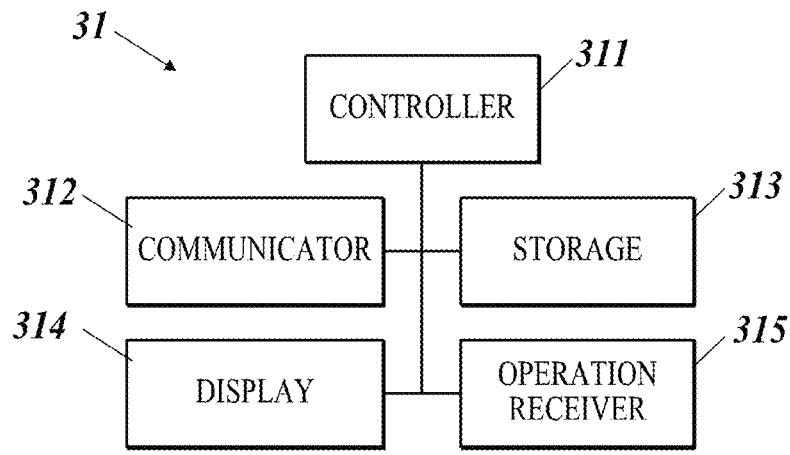
FIG. 4 is a block diagram showing an imaging control device (irradiation device control console) constituting the radiographic imaging system in FIG. 1 to FIG. 3.
Figure 5:
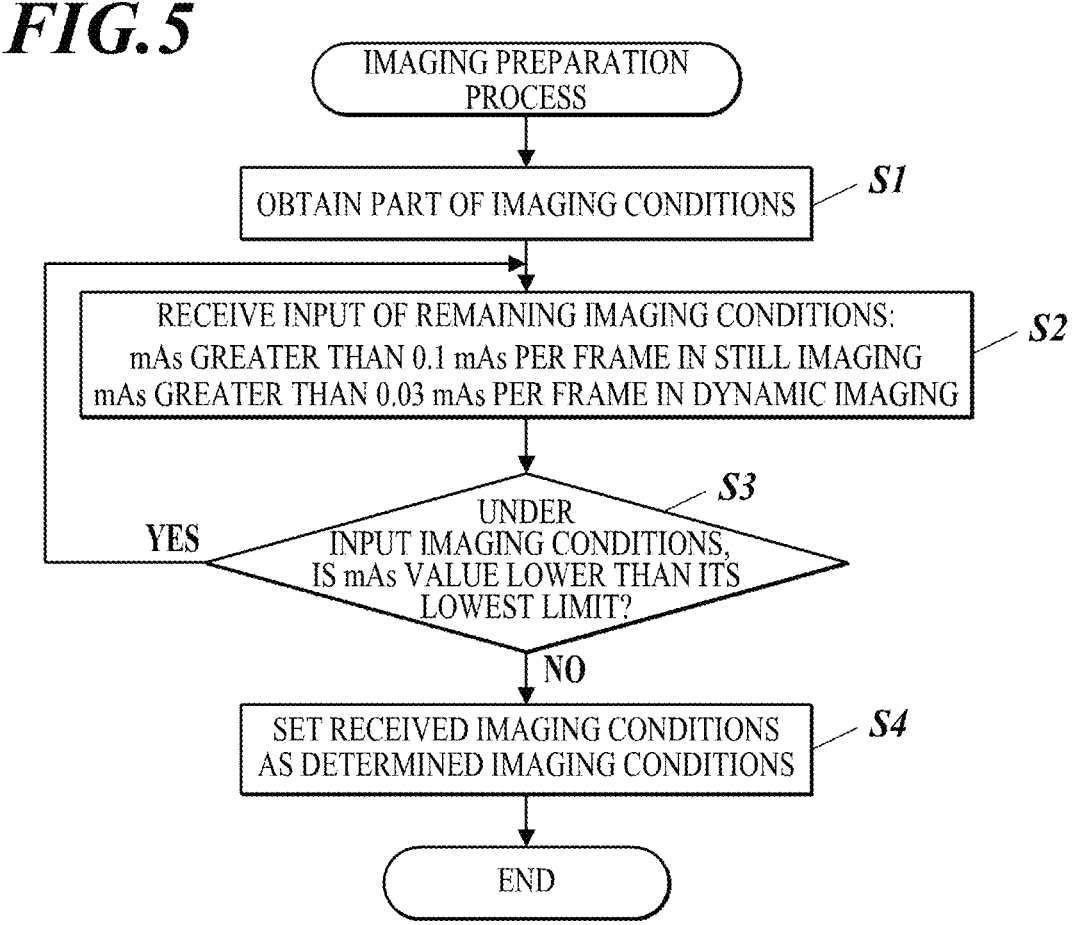
FIG. 5 is a flowchart showing the flow of an imaging preparation process to be performed by the imaging control device shown in FIG. 4.

FIG. 4 shows a block diagram of the irradiation device control console 31. FIG. 5 is a flowchart showing the flow of the imaging preparation process to be performed by the irradiation device control console 31.

[2-1. Configuration]

The irradiation device control console 31 includes a controller 311, a communicator 312, a storage 313, a display 314, and an operation receiver 315, as shown in FIG. 5.

The controller 311 includes a CPU and a RAM.

The CPU of the controller 311 reads various programs stored in the storage 313, loads the programs into the RAM, and performs various processes including the imaging preparation process to be described later in accordance with the loaded programs. The CPU of the controller 311 thus centrally controls operation of the components of the irradiation device control console 31.

The communicator 312 is constituted of a wired or wireless communication module, for example. The communicator 312 is capable of exchanging various signals and various kinds of data with the other devices (e.g., the irradiation device 1, the detector 2) wirelessly or via a cable over the communication network N.

The storage 313 is constituted of a nonvolatile semiconductor memory, a hard disk, or the like.

The storage 313 stores a program(s) for the controller 311 to perform various processes and parameters required for executing the program. The program is for controlling the system 100 (mobile radiographic imaging apparatus).

The storage 313 in this embodiment is capable of storing image data of radiographic images.

The image data may be stored in a storage different from the storage 313.

The display 314 is constituted of a monitor, such as a liquid crystal display (LCD) or a cathode ray tube (CRT), and displays various images and various kinds of information in accordance with commands of display signals input by the controller 311.

The display 314 may perform display in accordance with commands of display signals input by the detector control console 32.

The operation receiver 315 is configured to be operable by the user.

The operation receiver 315 includes a keyboard having cursor keys, number keys, and various function keys, a pointing device such as a mouse, and a touchscreen layered on a surface of the display 314.

The operation receiver 315 outputs control signals to the controller 311 on the basis of the operation made by the user.

The operation receiver 315 may output control signals to the detector control console 32 on the basis of the operation made by the user.

When the detector control console 32 includes a display, the irradiation device control console 31 may not include the display 314. In such a case, the display of the detector control console 32 may perform display in accordance with display signals output by the controller 311.

When the detector control console 32 includes an operation receiver, the irradiation device control console 31 may not include the operation receiver 315. In such a case, the controller 311 may receive control signals corresponding to the operation made on the operation receiver of the detector control console 32.

The irradiation device control console 31 and the detector control console 32 may each include a display and an operation receiver.

[2-2. Operation]

When a predetermined condition is met, the controller 311 of the irradiation device control console 31 configured as described above performs the imaging preparation process exemplified in FIG. 5.

Examples of the predetermined condition include (i) the irradiation device control console 31 is turned on, (ii) the irradiation device control console 31 receives a predetermined control signal from the other device, and (iii) the operation receiver 315 receives a predetermined operation.

In the imaging preparation process, the controller 311 firstly performs an obtaining step (Step S1).

In the obtaining step, the controller 311 obtains information on part of imaging conditions from the detector control console 32. The part of imaging conditions includes all, some, or any of the following: the type of radiographic image (still image or dynamic image), the frame rate, the imaging part, the SID, the maximum number of frames, presence or absence of an additional filter, and presence or absence of a radiographic grid.

The controller 311 may directly receive at least any of the part of imaging conditions (conditions based on the operation made on the operation receiver 315), instead of obtaining the conditions from the detector control console 32.

After obtaining information on the part of imaging conditions, the controller 311 performs a receiving step (Step S2).

In the receiving step, the controller 311 receives the remaining imaging conditions (allows the operation receiver 315 to receive input operations).

The remaining conditions include the irradiation current and the irradiation time.

In receiving input of the remaining imaging conditions, when the user operates the operation receiver 315, the controller 311 changes the default value of at least either the irradiation current or the irradiation time in response to the operation made on the operation receiver 315.

For example, when the type of radiographic image is dynamic image and the frame rate is set to 15 fps, the irradiation current that can be input is within the range of 80 to 250 mA, and the irradiation time that can be input is within the range of 1 to 8 ms.

The product of the irradiation current (mA) and the irradiation time (s) is the mAs.

In this reception process, the controller 311 receives imaging conditions regarding the mAs.

In performing still imaging, the controller 311 receives imaging conditions regarding the mAs per frame in still imaging. In performing dynamic imaging, the controller 311 receives imaging conditions regarding the mAs per frame in dynamic imaging.

The lower limit of the mAs per frame in still imaging and the lower limit of the mAs per frame in dynamic imaging are fixed.

In this embodiment, the lower limit of the mAs per frame in still imaging that can be input with the irradiation device control console 31 is 0.1 mAs, and the lower limit of the mAs per frame in dynamic imaging that can be input with the irradiation device control console 31 is 0.03 mAs.

That is, the lower limit of the mAs per frame in dynamic imaging that can be input with the irradiation device control console 31 is lower than the lower limit of the mAs per frame in still imaging that can be input with the irradiation device control console 31.

For example, assume that: the type of radiographic image is dynamic image; the input irradiation current is 80 mA; and the irradiation time is 1 ms (0.001 s). In the case, the mAs per frame is: 80×0.001=0.08 mAs, which is lower than 0.1 mAs.

In the receiving step, the controller 311 may be configured to display default values of the irradiation current and the irradiation time on the display 314.

The remaining imaging conditions that are to be received may include the tube voltage.

The remaining imaging conditions that are to be received may further include the mAs. That is, the controller 311 may receive the input of the mAs itself, instead of receiving the input of the irradiation current and the irradiation time.

In such a case, the controller 311 may receive: the input of the mAs and the irradiation current; or the input of the mAs and the irradiation time.

In the receiving step, the controller 311 may set beforehand (automatically) the lower limit of the mAs per frame in dynamic imaging, on the basis of at least one among the frame rate, the imaging part, the tube current, the SID, the maximum number of frames, presence or absence of an additional filter, and presence or absence of a radiographic grid.

The controller 311 may automatically set beforehand such a mAs per frame in to-be-performed dynamic imaging that is greater than the lower limit, on the basis of at least one among the abovementioned imaging conditions.

The lower limit for the mAs per frame in dynamic imaging may be selected from multiple lower limits.

In the case, the controller 311 may switch the lower limits according to the obtained part of imaging conditions (e.g., imaging part, frame rate) in the receiving step.

After receiving the input of the remaining imaging conditions, the controller 311 performs a determining step (Step S3).

In the determining step, the controller 311 determines whether the mAs is lower than the lower limit under the input imaging condition(s).

In the determining step, when determining that the mAs per frame in still imaging is lower than the lower limit thereof under the input imaging condition or determining that the mAs per frame in dynamic imaging is lower than the lower limit thereof under the input imaging condition (Step S3: Yes), the controller 311 returns to Step S2.

Thus, the controller 311 does not set the imaging condition under which the mAs per frame in still imaging is lower than 0.1 mAs or the imaging condition under which the mAs per frame in dynamic imaging is lower than 0.03 mAs.

In the determining step, when determining that the mAs is lower than the lower limit under the input imaging condition (Step S3: Yes), the controller 311 may not return to Step S2 but instead may end the imaging preparation process.

In the determining step, when determining that the mAs per frame in still imaging is not lower than the lower limit thereof (0.1 mAs) or determining that the mAs per frame in dynamic imaging is not lower than the lower limit thereof (0.03 mAs) (Step S3: No), the controller 311 performs the setting step (Step S4).

In the setting step, the controller 311 sets the imaging condition received in the receiving step as the determined imaging condition.

More specifically, the controller 311 sends the determined imaging condition to the radiation control device 11 via the communicator 312. When the determined imaging condition affects the operation of the detector 2, the controller 311 sends the determined imaging condition to the detector control console 32. When the determined imaging condition does not affect the operation of the detector 2, the controller 311 does not send the determined imaging condition to the radiation control console 32.

When receiving the determined imaging condition, the detector control console 32 sends the received condition to the additional device 5. When receiving the determined imaging condition, the additional device 5 sends the received condition to the detector 2.

The devices that have received the determined imaging condition (irradiation device 1, detector 2, and so forth) operate according to the received imaging condition.

In the determining step, when determining that the mAs is lower than the lower limit thereof under the input imaging condition (Step S3: Yes), the controller 311 may perform a notifying step at least: before returning to Step S2: while returning to Step S2; or while performing Step S2 after returned to Step S2.

In the notifying step, the controller 311 notifies that the input imaging condition cannot be set.

In the notifying step in this embodiment, the controller 311 performs the notification by displaying, on the display 314, a literal or pictorial notification indicating that the input imaging condition cannot be set.

The controller 311 may perform the notification by outputting a voice/sound indicating that the input cannot be set from a not-illustrated speaker or by lighting a lamp in a way indicating that the input cannot be set (e.g., color or blinking of light).

By performing the imaging preparation process described above, the controller 311 sets the imaging condition regarding the mAs per frame in still imaging or the imaging condition regarding the mAs per frame in dynamic imaging.

Further, depending on the irradiation current and irradiation time input by the user in the receiving step, the controller 311 can set the imaging condition under which the mAs per frame in dynamic imaging is higher than 0 and lower than 0.1 (0<mAs<0.1).

Performing the imaging preparation process corresponds to allowing the imaging condition to be set in the method.

<3. Advantageous Effects>

The exposure dose (unit: Gy) is expressed by the following formula (1).

$$\text{Exposure dose} = \text{Coefficient for tube current and total filtration} \times \text{mAs} \times (1/\text{distance to entrance surface})^2 \quad (1)$$

For example, assume that dynamic imaging of the chest region is performed in the anterior-posterior view in a radiography room under the following imaging conditions.

According to the above formula (1), the exposure dose in this imaging is approximately 0.28 mGy, which is below 0.3 mGy specified in the exposure guideline (DRLs) and therefore conforms to the DRLs.

[Imaging conditions] SID: 200 centimeters, tube current: 80 kV; mAs: 0.31 mAs, frame rate: 15 fps; imaging time: 8 seconds, additional filter: Cu 0.2 mm+Al 0.1 mm On the other hand, in imaging with a mobile medical vehicle or imaging the lying subject, the SID is generally shorter than in imaging in a radiography room.

For example, when dynamic imaging of the chest region is performed in the anterior-posterior view with the SID shortened to 100 centimeters (the other imaging conditions are the same as in imaging in a radiography room), the exposure dose is approximately 1.12 mGy, which is far beyond 0.3 mGy specified in DRLs.

The system 100 (irradiation device control console) includes the controller 311 capable of setting the imaging conditions under which the mAs per frame in dynamic imaging is lower than 0.1 mAs.

Therefore, even when the SID is set to 100 centimeters, the controller 311 lowers the mAs to, for example, 0.09 mAs (the other imaging conditions are the same as in imaging in a radiography room) to dynamically image the chest region in the posterior-anterior view. This yields the exposure dose of approximately 0.27 mGy, which is lower than 0.3 mGy specified in DRLs and therefore conforms to DRLs.

In DRLs, the wrist is set to have the lowest exposure dose, which is 0.1 mGy (one third of the exposure dose for the chest region).

Under the above-described conditions, the exposure dose for the wrist exceeds DRLs.

According to the system 100, the mAs is lowered to 0.03 mAs, for example (the imaging conditions other than the SID and the mAs are the same as in imaging in a radiography room) to dynamically image the wrist. This results in the exposure dose of approximately 0.09 mGy, which is lower than 0.1 mGy specified in DRLs and therefor conforms to DRLs.

Thus, the system 100 (irradiation device control console) can appropriately perform dynamic imaging even when the maximum SID or the maximum heat unit value of the radiation source 12 is limited.

Although the embodiment of the present invention has been described and illustrated in detail, the scope of the present invention is not limited to the embodiment described above but encompasses the scope of the invention recited in the claims and the equivalent thereof.

What is claimed is:

1. A mobile radiographic imaging apparatus that performs dynamic imaging by using radiation to obtain a dynamic image constituted of multiple frames and that performs still imaging by using radiation to obtain a still image constituted of a single frame, the apparatus comprising:
   a first hardware processor that allows the apparatus to perform the dynamic imaging in which a mAs per frame is less than 0.1 mAs and that does not allow the apparatus to perform the still imaging in which a mAs per frame is less than 0.1 mAs.

2. The mobile radiographic imaging apparatus according to claim 1, wherein the first hardware processor is capable of setting an imaging condition under which the mAs per frame in the dynamic imaging is less than 0.1 mAs.

3. The mobile radiographic imaging apparatus according to claim 2, wherein the imaging condition includes an irradiation current and an irradiation time.

4. The mobile radiographic imaging apparatus according to claim 2, wherein the imaging condition includes a mAs.

5. The mobile radiographic imaging apparatus according to claim 2, wherein
in response to receiving an input of the imaging condition under which the mAs is less than a lower limit of the mAs per frame in the dynamic imaging, the first hardware processor causes a display, a speaker, or a lamp to notify that the input imaging condition is unable to be set.

6. The mobile radiographic imaging apparatus according to claim 1, wherein a lower limit of the mAs per frame in the dynamic imaging is fixed.

7. The mobile radiographic imaging apparatus according to claim 6, wherein the lower limit of the mAs per frame in the dynamic imaging is 0.03 mAs.

8. The mobile radiographic imaging apparatus according to claim 1, wherein a lower limit of the mAs per frame in the dynamic imaging is selected from among multiple values.

9. The mobile radiographic imaging apparatus according to claim 8, wherein the first hardware processor determines the lower limit of the mAs per frame in the dynamic imaging, based on at least one among:
a frame rate;
an imaging part;
a tube voltage;
a distance between a radiation source and a radiation detector that detects the radiation;
a maximum number of frames;
presence or absence of an additional filter; and
presence or absence of a radiographic grid.

10. The mobile radiographic imaging apparatus according to claim 1, further comprising a radiation source that emits the radiation.

11. The mobile radiographic imaging apparatus according to claim 10, wherein a maximum distance between the radiation source and a floor is equal to or less than 200 centimeters.

12. The mobile radiographic imaging apparatus according to claim 10, further comprising a second hardware processor that controls the radiation source based on the imaging condition set by the first hardware processor.

13. The mobile radiographic imaging apparatus according to claim 1, wherein
the first hardware processor does not set an imaging condition under which the mAs per frame in the still imaging is less than 0.1 mAs.

14. A non-transitory computer-readable storage medium storing a program that controls a mobile radiographic imaging apparatus configured to perform dynamic imaging by using radiation to obtain a dynamic image constituted of multiple frames and configured to perform still imaging by using radiation to obtain a still image constituted of a single frame, wherein
the program allows the apparatus to perform the dynamic imaging in which a mAs per frame is less than 0.1 mAs, and
the program does not allow the apparatus to perform the still imaging in which a mAs per frame is less than 0.1 mAs.

15. A method for controlling a mobile radiographic imaging apparatus that performs dynamic imaging by using radiation to obtain a dynamic image constituted of multiple frames and that performs still imaging by using radiation to obtain a still image constituted of a single frame, the method comprising:
allowing the apparatus to perform the dynamic imaging in which a mAs per frame is less than 0.1 mAs, and
not allowing the apparatus to perform the still imaging in which a mAs per frame is less than 0.1 mAs.

16. A control apparatus of an irradiation apparatus that emits radiation for dynamic imaging in which a dynamic image constituted of multiple frames is obtained and for still imaging in which a still image constituted of a single image is obtained, the control apparatus comprising:
a hardware processor that allows the dynamic imaging in which a mAs per frame is less than 0.1 mAs and that does not allow the still imaging in which a mAs per frame is less than 0.1 mAs.

17. A radiographic imaging system comprising:
the control apparatus according to claim 16; and
a radiation source that emits the radiation.

* * * * *